(12) United States Patent
Mahaffey et al.

(10) Patent No.: US 8,608,755 B2
(45) Date of Patent: Dec. 17, 2013

(54) DERMATOME WITH WIDTH PLATE CAPTURES

(75) Inventors: Mark Mahaffey, New Philadelphia, OH (US); Bruce Straslicka, Medina, OH (US)

(73) Assignee: Zimmer Surgical, Inc., Dover, OH (US)

( * ) Notice: Subject to any disclaimer, the term of this patent is extended or adjusted under 35 U.S.C. 154(b) by 117 days.

(21) Appl. No.: 13/180,925

(22) Filed: Jul. 12, 2011

(65) Prior Publication Data

US 2013/0018390 A1    Jan. 17, 2013

(51) Int. Cl.
*A61B 17/50* (2006.01)

(52) U.S. Cl.
USPC ....................................... 606/132

(58) Field of Classification Search
USPC ............ 606/131, 132, 133; 30/32, 50, 51, 52, 30/53, 54, 55, 57, 58, 59, 60, 60.5, 61, 62, 30/63, 64, 65, 77, 78, 79, 80, 81, 82, 83, 30/329, 337, 339, 340, 342
See application file for complete search history.

(56) References Cited

U.S. PATENT DOCUMENTS

| | | | |
|---|---|---|---|
| 2,457,772 A | 12/1948 | Milford et al. | |
| 3,428,045 A | 2/1969 | Kratzsch | |
| 3,583,403 A | 6/1971 | Keller et al. | |
| 3,670,734 A | 6/1972 | Hardy | |
| 3,820,543 A | 6/1974 | Vanjushin | |
| 3,857,178 A | 12/1974 | Stevens | |
| 4,038,986 A | 8/1977 | Mahler | |
| 4,098,278 A | 7/1978 | Schwartz | |
| 4,257,160 A * | 3/1981 | Murai ........................... 30/41 |
| 4,754,756 A | 7/1988 | Shelanski | |
| 4,917,086 A | 4/1990 | Feltovich | |
| 5,873,881 A | 2/1999 | McEwen et al. | |
| 2004/0225309 A1 | 11/2004 | Eriksson et al. | |
| 2009/0157095 A1 | 6/2009 | Barker et al. | |
| 2009/0157096 A1 | 6/2009 | Boles | |

FOREIGN PATENT DOCUMENTS

| | | |
|---|---|---|
| FR | 2148916 A5 | 3/1973 |
| GB | 1048353 A | 11/1966 |

* cited by examiner

*Primary Examiner* — Ryan Severson
*Assistant Examiner* — Jonathan W Miles
(74) *Attorney, Agent, or Firm* — Seager, Tufte & Wickhem, LLC

(57) ABSTRACT

A dermatome having a main body, a blade assembly and a bottom member, where the main body includes a bottom surface and at least one capture extending from the bottom surface. The bottom member may be inserted into the at least one capture and fastened to the main body, where the blade assembly may be mounted between the fastened bottom member and the bottom surface of the main body. The captures of the main body may limit the movement of the inserted bottom member in at least three general directions and the fastener may limit the movement of the bottom member in at least a fourth general direction.

18 Claims, 10 Drawing Sheets

DERMATOME WITH WIDTH PLATE CAPTURES

TECHNICAL FIELD

The disclosure is directed to dermatomes for surgically harvesting grafts of skin. More particularly, the disclosure is directed to dermatomes including width plate capture structures.

BACKGROUND

Conventional dermatomes are used for cutting skin tissue to obtain transplantable skin grafts. A skin graft is a patch of healthy skin that is harvested from one area of the body or donor site to cover a damaged or skinless area of the body. Typically, a dermatome has a front end holding a flat blade to be placed in contact with a tissue surface and a motor to oscillate the blade from side to side to create a slicing action which cuts the tissue as the dermatome is moved along the tissue surface.

SUMMARY

The disclosure is directed to several alternative designs, materials and methods of manufacturing medical device structures and assemblies. Although it is noted that conventional dermatomes exist, there exists a need for improvement on those devices.

Accordingly, one illustrative embodiment of the disclosure may include a dermatome with a main body having a bottom surface, a first capture and a second capture, where the captures may extend from the bottom surface and the second capture may be spaced across the main body from the first capture. The dermatome may also include a blade assembly having a first side facing the bottom surface of the main body and a second side opposite the first side. The dermatome may further include a bottom member facing the second side of the blade assembly and communicating with the first and second captures of the main body. The captures may operate to prevent movement of the bottom member in opposing first and second lateral directions and at least a third direction perpendicular to the first and second lateral directions.

The above summary of some example embodiments is not intended to describe each disclosed embodiment or every implementation of the disclosure.

BRIEF DESCRIPTION OF THE DRAWINGS

The disclosure may be more completely understood in consideration of the following detailed description of various embodiments in connection with the accompanying drawings, in which.

Figure 1:
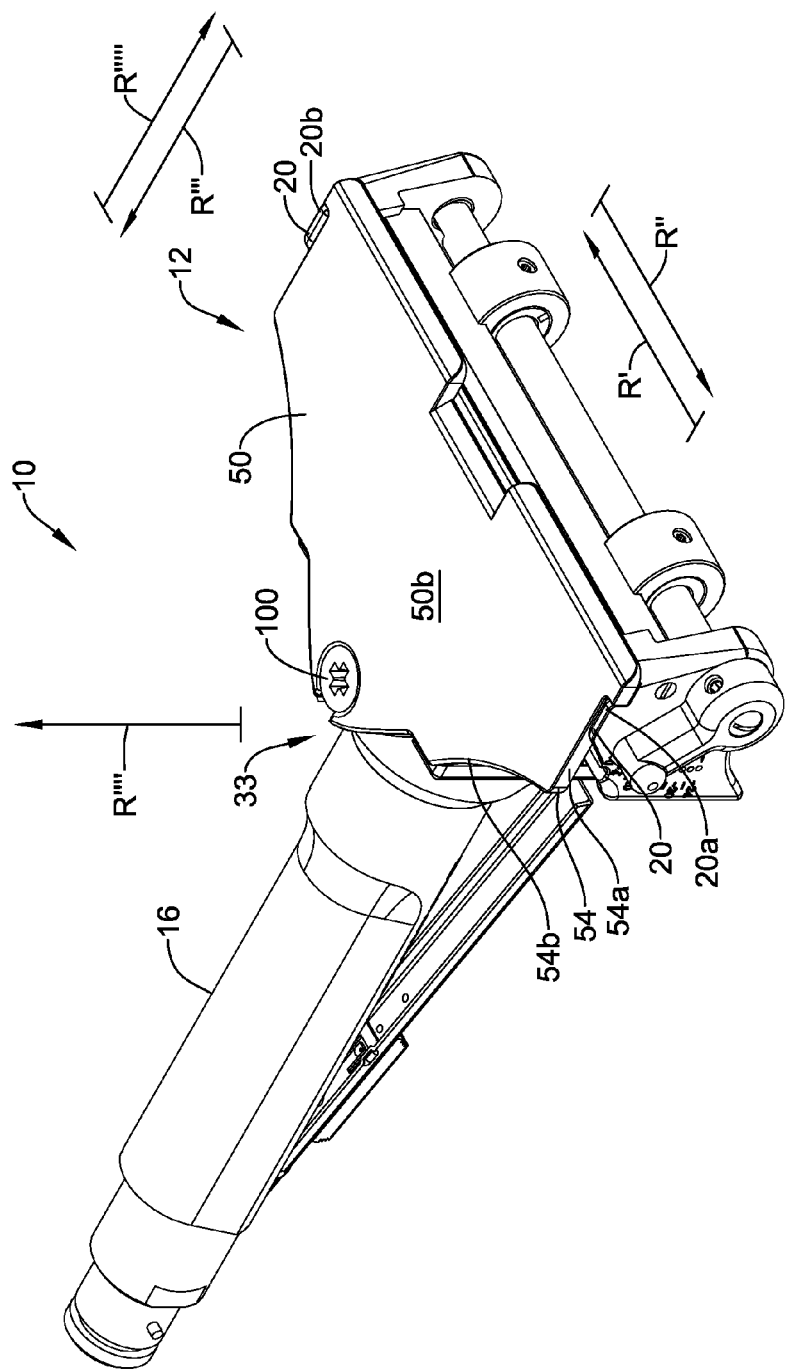
FIG. 1 is a perspective view of a dermatome according to an aspect of the disclosure.

While the disclosure is amenable to various modifications and alternative forms, specifics thereof have been shown by way of example in the drawings and will be described in detail. It should be understood, however, that the intention is not to limit aspects of the claimed disclosure to the particular embodiments described. On the contrary, the intention is to cover all modifications, equivalents, and alternatives falling within the spirit and scope of the claimed disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the claimed disclosure. The illustrative embodiments depicted are intended only as exemplary. Selected features of any illustrative embodiment may be incorporated into an additional embodiment unless clearly stated to the contrary.

The present disclosure relates to the subject matter filed by inventors Mark Mahaffey and Bruce Straslicka and contained in the U.S. patent application titled DERMATOME BLADE ASSEMBLY GUARD having application Ser. No. 13/180,977 and the U.S. patent application titled DERMATOME BLADE ASSEMBLY having application Ser. No. 13/180,831, both filed on Jul. 12, 2011, and which are both expressly incorporated herein by reference in their entirety.

Referring to FIGS. 1-10, a dermatome 10 for harvesting grafts of skin tissue may have a main body 12 connected to a handle 16. Dermatome 10 may include a blade assembly 40 mounted on main body 12, as well as a bottom member 50 engaging a bottom surface 18 of main body 12. In some instances, bottom member 50 may be a width plate capable of controlling the width of the skin tissue to be cut by a blade 42 of blade assembly 40. Dermatome 10 may include a set of bottom members 50 (e.g., a plurality of width plates), where each width plate allows for a cut of tissue having a different width. Alternatively or in addition, dermatome 10 may include at least one adjustable bottom member 50 (e.g., width plate) capable of allowing various widths of tissue to be cut by blade 42, where the width plate may be adjusted by a user or other party to harvest a desired width of the skin tissue.

Blade assembly 40 may include a blade 42 and a blade mount 44, where blade 42 and blade mount 44 may be interconnected. Blade assembly 40 may be mounted on main body 12 by being fitted between bottom surface 18 and bottom member 50 or may be positioned or mounted adjacent or to main body 12 in any other manner known in the mounting art. Blade assembly 40 may be mounted to main body 12 so as to be fixed with respect to main body 12 or so as to allow blade assembly 40 to move in at least a first direction R' and second direction R" with respect to main body 12. Second direction R" may be a direction substantially opposite first direction R' or any other direction not identical to first direction R'. For example, where second direction R" is a direction substantially parallel to and opposite first direction R', blade assembly may be made to reciprocate in first and second directions R', R".

Figure 2:
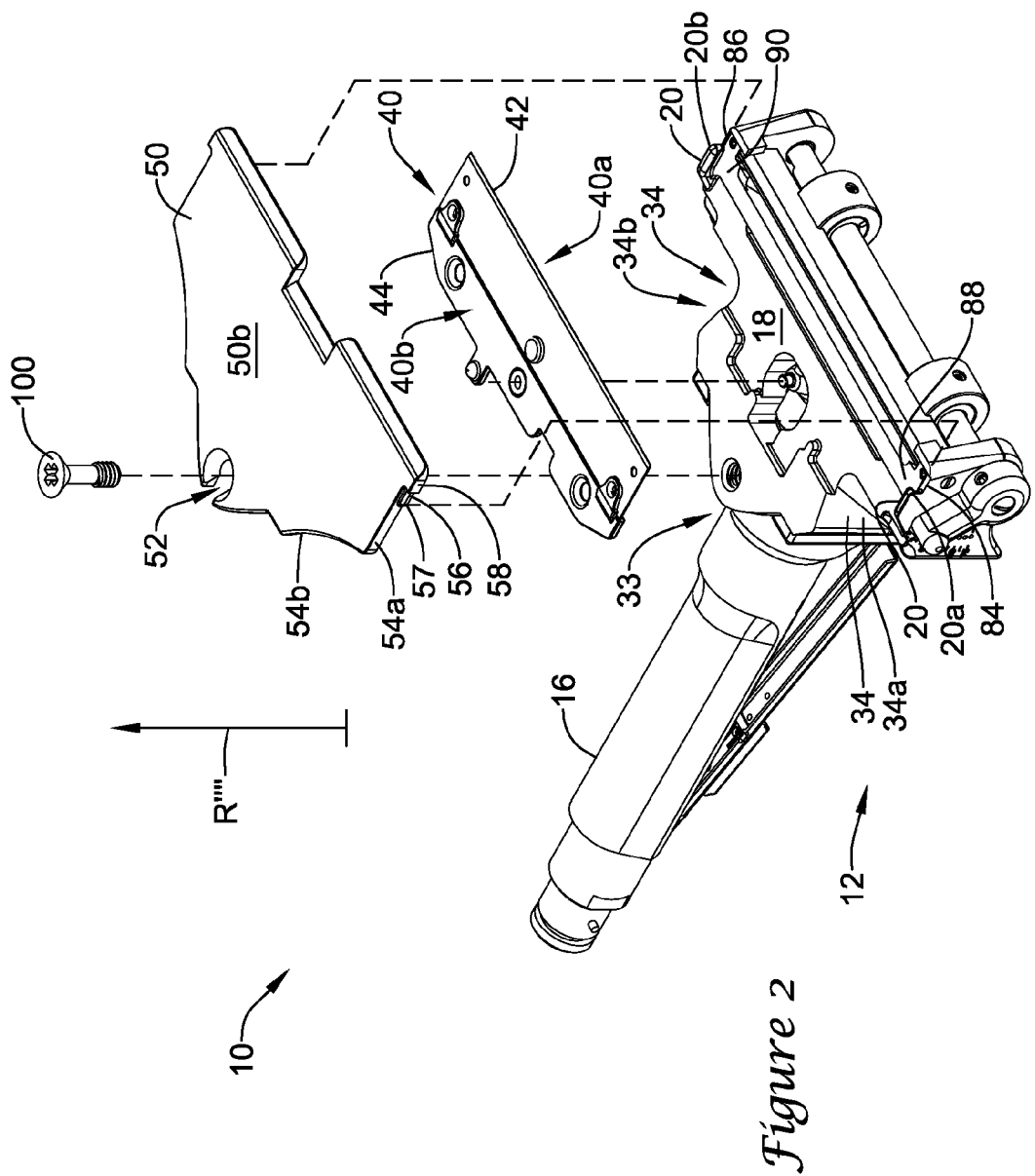
FIG. 2 is an exploded perspective view of a dermatome according to an aspect of the disclosure.
Figure 3:
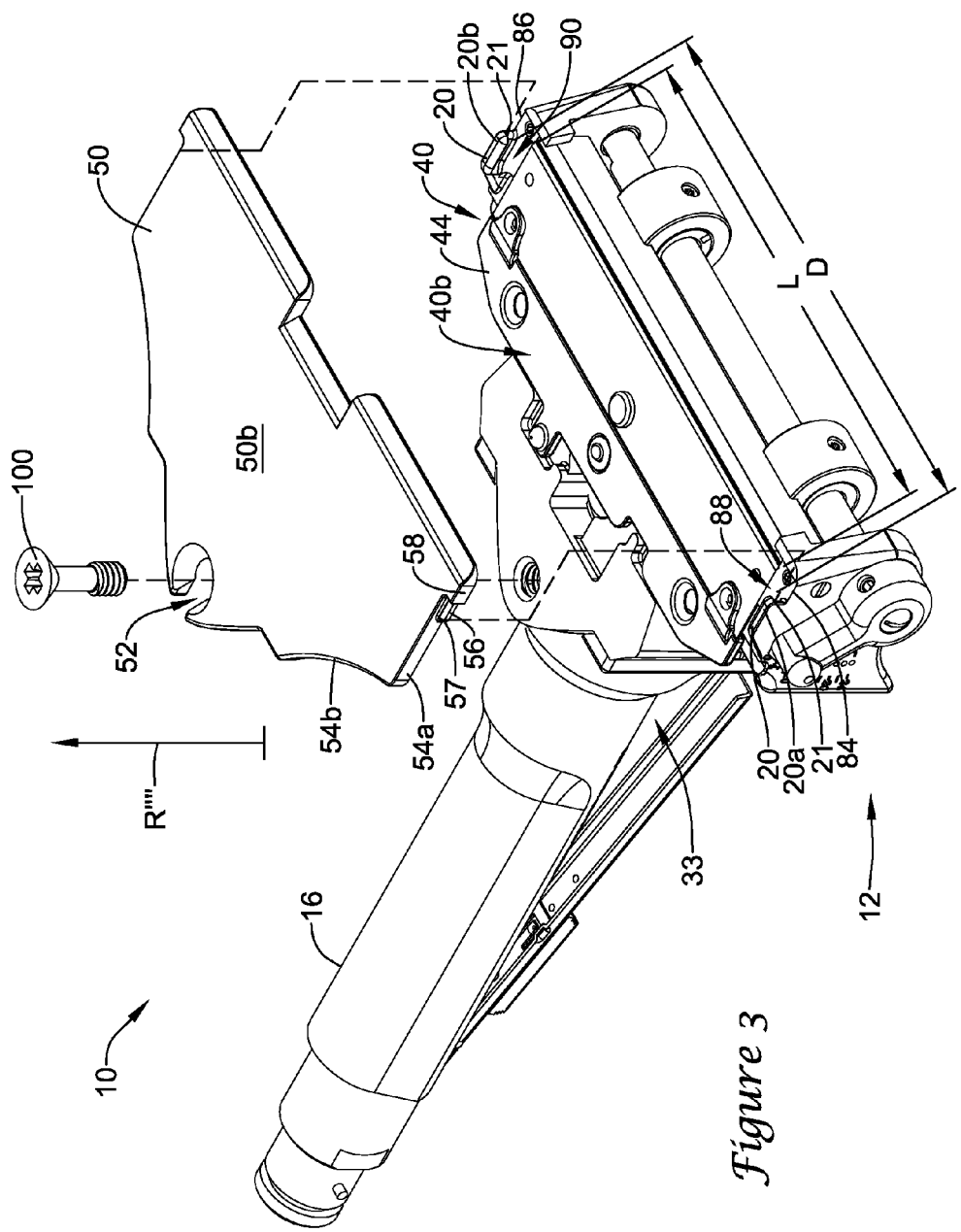
FIG. 3 is a perspective view of the dermatome of FIG. 1 with a bottom member removed.

Although blade assembly 40 may be mounted to main body 12 in any manner, dermatome 10 may include, for example, a system for mounting blade assembly 40 to bottom surface 18 of main body 12 utilizing bottom member 50, where bottom member 50 faces blade assembly 40, as seen in FIGS. 2 and 3. In the example, blade assembly 40 may be positioned so as to have a first side 40a facing and/or contacting bottom surface 18 and a second side 40b facing and/or contacting a first side 50a of bottom member 50. The contact between blade assembly 40, main body 12 and bottom member 50 may allow for movement of blade assembly 40 in at least first and second directions R', R", while preventing movement of blade assembly 40 in a direction of a plane perpendicular to a plane defining a second side 50b of bottom member 50, where second side 50b is substantially parallel to and opposite first side 50a and directions R', R".

As seen in FIGS. 1-5, 8 and 9, main body 12 may have at least one capture 20 extending from bottom surface 18 for engaging bottom member 50. For example, main body 12 may have a first capture 20a and a second capture 20b extending from bottom surface 18, where first capture 20a may be spaced across bottom surface 18 from second capture 20b. In the example, first capture 20a may be located at or proximate a first edge 84 of a first side 88 of bottom surface 18 and second capture 20b may be located at or proximate a second edge 86 of a second side 90 of bottom surface 18, where second side 90 may be opposite first side 88. Distance D between first capture 20a and second capture 20b may be longer than a length L of blade assembly 40 such that blade assembly 40 fits within a space on bottom surface 18 between first capture 20a and second capture 20b. Alternatively, length L and distance D may take on any other set of dimensions, related or otherwise. For example, where length L may have a dimension greater than distance D, blade assembly 40 may have provisions for allowing captures 20a, 20b to extend there through or captures 20a, 20b may extend around blade assembly 40.

First and second captures 20a, 20b, or other capture(s) 20, may be any shape and size or dimension capable of receiving bottom member 50 and limiting or preventing movement of bottom member 50 in two or more directions. For example, the features of captures 20a, 20b may limit movement of bottom member 50 through lateral stop 28 limiting movement in lateral first direction R', a second oppositely positioned lateral stop 28 limiting movement in lateral second direction R" substantially planar and opposite lateral first direction R', and back stops 26 limiting movement of bottom member 50 in a third direction R'" substantially planar and perpendicular to first and second directions R', R". First, second and third directions R', R", R'" may be substantially planar or substantially parallel to a plane along second side 50b of bottom member 50, or both. In addition, captures 20 may limit or prevent movement of bottom member 50 in a general fourth direction R"", where fourth direction R"" may be a direction that is not parallel to any of the first, second and third directions R', R", R'". For example, fourth direction R"" may be a direction substantially perpendicular to first, second and third directions R', R", R'".

Figure 4:
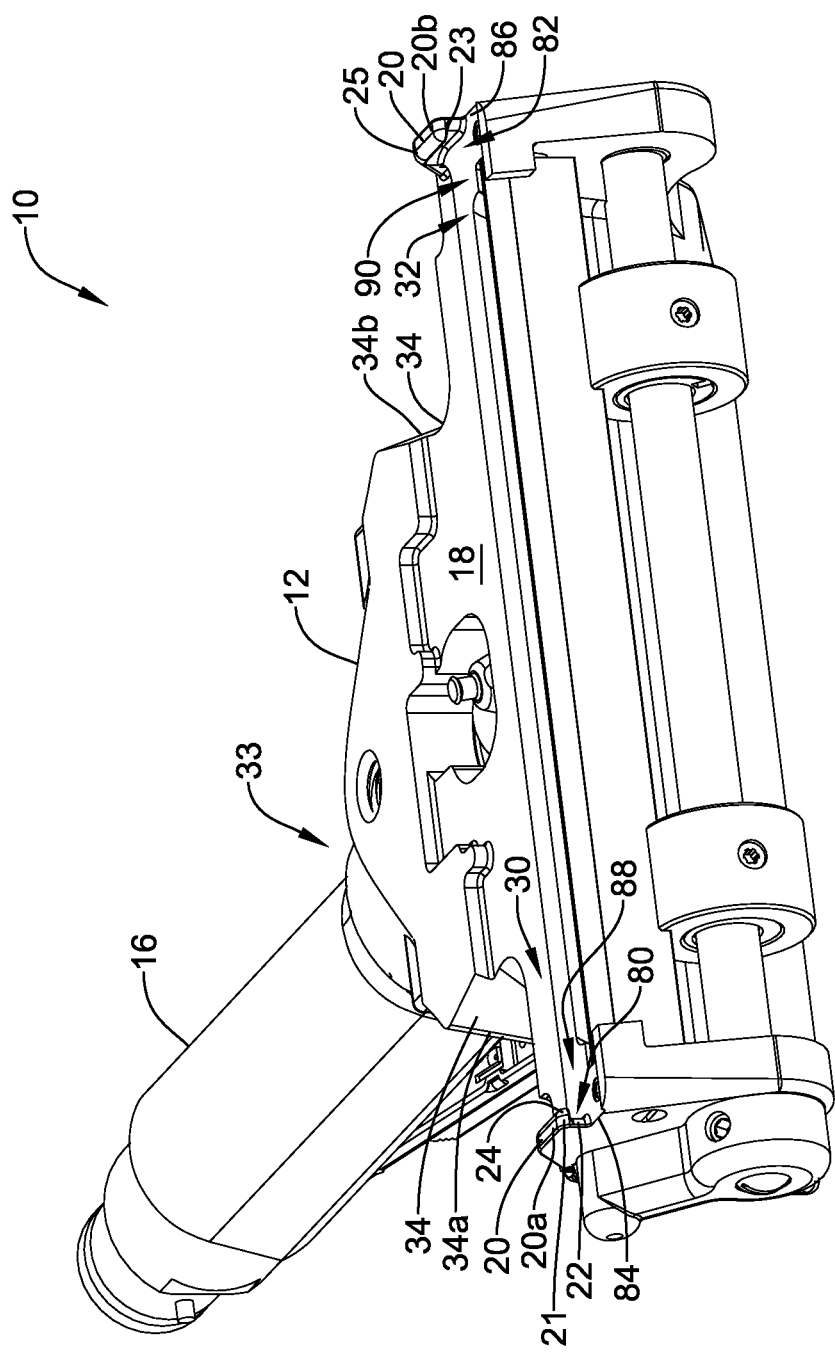
FIG. 4 is a perspective view of certain features of a main body of a dermatome according to an aspect of the disclosure.
Figure 5:
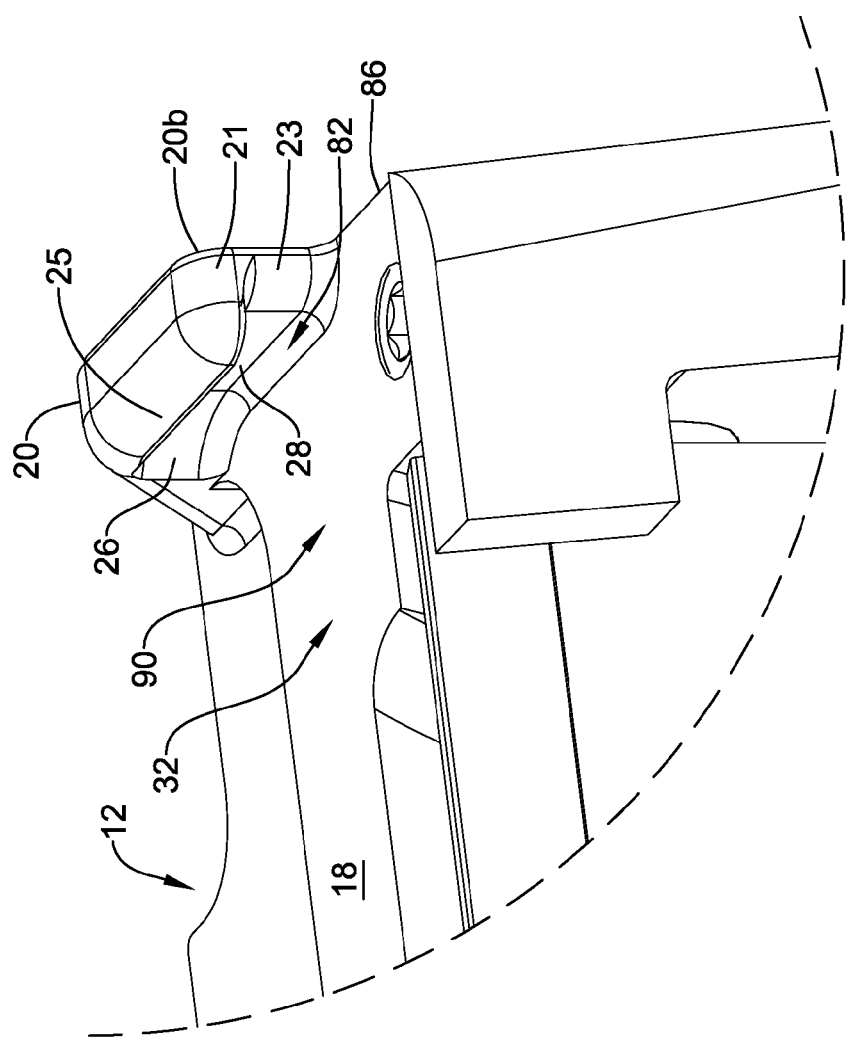
FIG. 5 is a magnified view of certain features of the dermatome depicted in FIG. 4.

Structurally, as seen in FIGS. 4 and 5, first capture 20a may include a first extension 22 extending from bottom surface 18 of main body 12 to a first cover 24. First extension 22 may include a lateral stop 28 and a back stop 26, where a bottom of lateral stop 28 and a bottom of back stop 26 may extend from bottom surface 18 to first cover 24. First capture 20a may form a first capture slot 80 at least partially defined by bottom side or surface 18, side or lateral stop 28, back stop 26 and first top or cover 24, where first capture slot 80 may be capable of receiving at least a portion of bottom member 50 (e.g., a first capture profile 57). Second capture 20b may substantially mirror first capture 20a, as depicted in FIG. 4, or may take on any other dimension or orientation. For example, where second capture 20b may mirror first capture 20a, second capture 20b may include a second extension 23 extending from bottom surface 18. In the example, second extension 23 may include another lateral stop 28 and another back stop 26, where a bottom of both stops 26, 28 may extend from bottom surface 18 to a second cover 25. Second capture 20b may form a second capture slot 82 at least partially defined by bottom side or surface 18, side or lateral stop 28, back stop 26 and second top or cover 25, where second capture slot 82 may be capable of receiving at least a portion of bottom member 50 (e.g., a second capture profile 59). Although illustratively described herein, captures 20 may take on any shape or size capable of engaging bottom member 50. For example, captures 20 may take on a shape or size capable of providing a slide engagement or snap engagement or any other engagement with bottom member 50.

Capture 20 may be a single capture 20 having a shape and size capable of limiting or preventing movement of bottom member 50 in lateral first direction R', lateral second direction R", and third direction R'". Alternatively, capture 20 may include two or more captures 20, where the two or more captures 20 may be identical or may have varying shapes and dimensions and are able to collectively limit or prevent movement of bottom member 50 in at least first, second and third directions R', R", R'". Further, capture(s) 20 may limit or prevent movement in at least a fourth direction R"", which may be a direction not parallel to first, second and third directions R', R", R'" and may be generally perpendicular to, or form a different angle with respect to, first, second and third directions R', R", R'".

Figure 6:
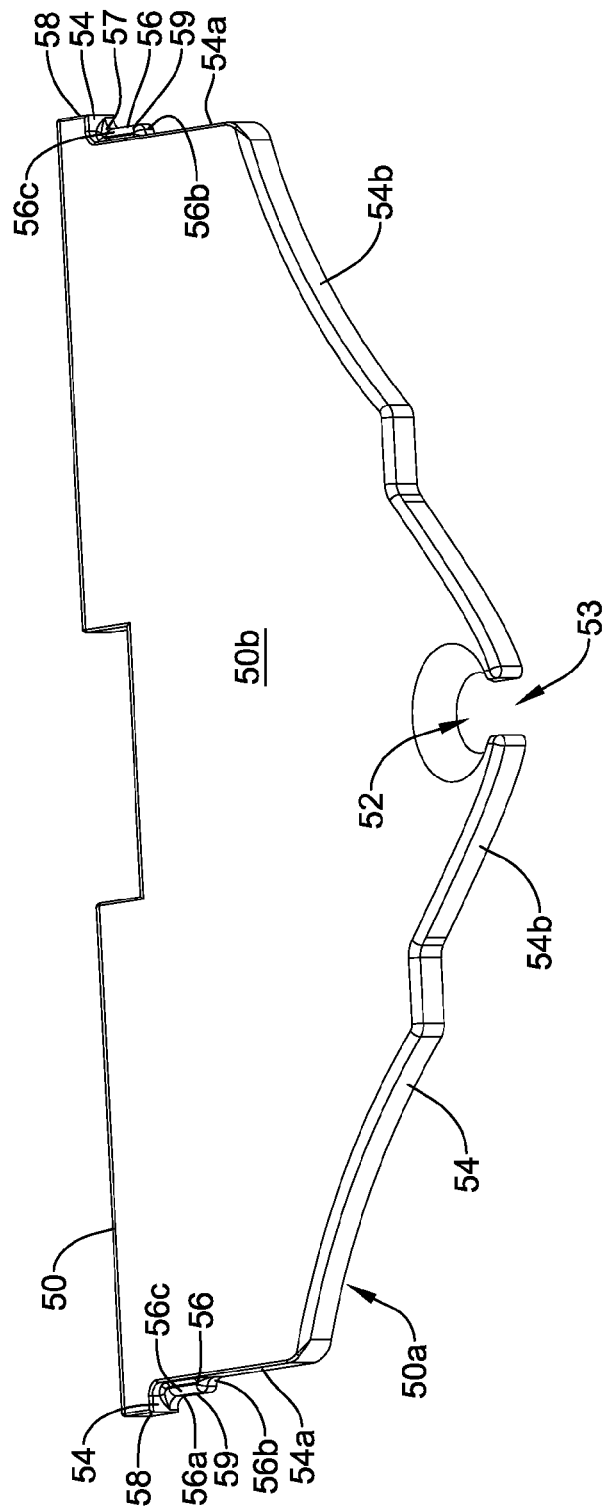
FIG. 6 is a perspective view of certain features of a bottom member of a dermatome according to an aspect of the disclosure.
Figure 7:
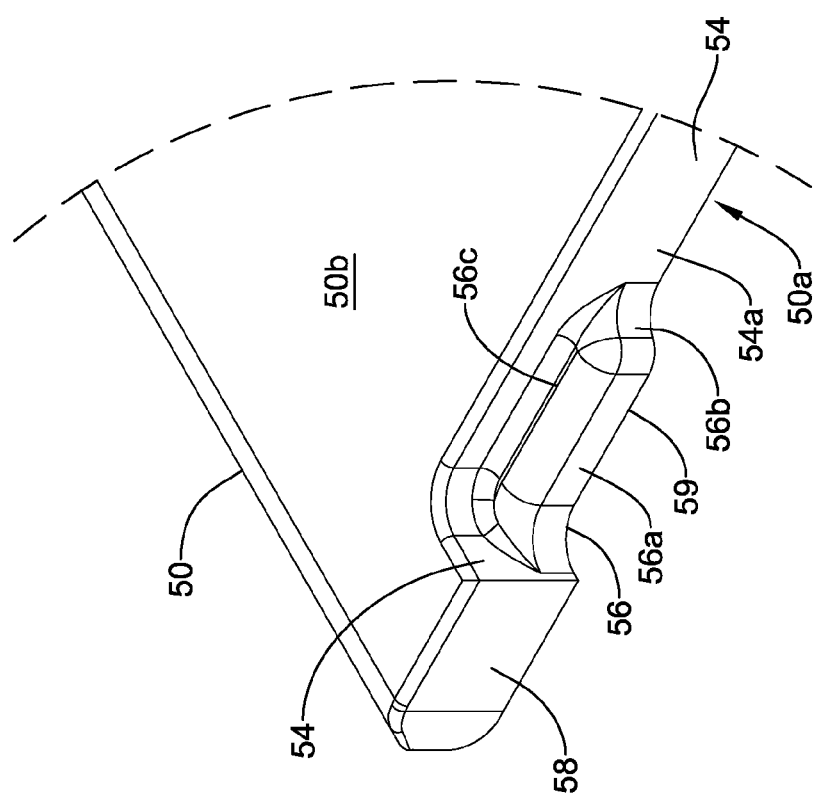
FIG. 7 is a magnified view of certain features of the dermatome depicted in FIG. 6.

As seen in FIGS. 6 and 7, bottom member 50 may have first side 50a and a second side 50b and at least one fastening hole 52. Fastening hole 52 may be at least partially defined by bottom member 50 and may extend from first side 50a to second side 50b. Fastening hole 52 may include a slot 53 extending laterally from an outer edge of bottom member 50 to intersect fastening hole 52 to allow a fastener 100 of appropriate size to be inserted into fastening hole 52 in a direction generally perpendicular to the longitudinal axis of fastening hole 52. In an illustrative embodiment, the at least one fastening hole 52 may be one and only one fastening hole 52 and that one and only one fastening hole 52 may be capable of receiving one and only one fastener 100, where fastener 100 may be inserted through fastening hole 52 and may engage main body 12 such as a threaded bore in main body 12. Fastener 100 may be any type of fastener. For example, fastener 100 may be a threaded fastener and may be capable of engaging complementary threads within a threaded bore 110 defined by main body 12. Engaged fastener 100 may be capable of limiting or preventing movement of bottom member 50 in first, second, third and fourth directions R', R", R'", R"", along with a fifth direction R'"". Fifth direction R'"" may be a direction substantially perpendicular to lateral first and second directions R', R", substantially opposite third direction R'", and substantially planar or parallel to first, second and third directions R', R", R'". Although directions R', R", R'", R"", R'"" are described as discrete directions, these directions may be general directions having particular relationships with respect to the other directions.

Bottom member 50 may further include capture profiles 56. Although two capture profiles 56 are depicted in FIG. 6, bottom member 50 may have any number of capture profiles. For example, bottom member 50 may have one capture profile 56 for each capture 20. As depicted in FIGS. 6 and 7, capture profiles 56 may have a particular shape and size, where the shape and size may be formulated to engage and be complementary to capture slots 80, 82 or slots of other captures 20. In an example of two capture profiles 56, first capture profile 57 may be substantially identical to second capture profile 59 as may be dictated by captures 20 or vice versa. That is, capture profiles 56 and captures 20 may have shapes and sizes that allow for respective capture profiles 56 and captures 20 to engage one another.

As seen in FIGS. 6 and 7, capture profiles 56 may be recessed from other portions of bottom member 50. A recessed capture profile 56 with respect to other portions of bottom member 50 may allow tops of covers 24, 25 to be flush or planar with second side 50*b* of bottom member 50, as seen in FIG. 1. Bottom member 50 may include a rear side 54 extending from first side 50*a* to second side 50*b*. As shown in FIGS. 6 and 7, capture profiles 56 may extend from rear side 54 along sides 54*a* or along a back 54*b* of rear side 54. In an illustrative embodiment, capture profiles 56 may include a side 56*a*, a back 56*b* and a top 56*c*. Side 56*a*, back 56*b* and top 56*c* may extend from rear side 54 and when capture profiles 56 are inserted into captures 20, sides 56*a* may be proximate lateral stops 28, backs 56*b* may be proximate back stops 26 and top 56*c* may be proximate first or second cover 24, 25. The locations and relationship of capture profiles 56 with respect to captures 20 may limit or prevent undesired movement of bottom member 50 in at least first, second and third directions R', R", R'".

As depicted in FIGS. 6 and 7, rear side 54 may have any shape and size. For example, rear side 54 may be substantially perpendicular to the plane along second side 50*b* of bottom member 50, where rear side 54 may form corners with first side 50*a* and second side 50*b* and may extend between terminal sides 58 of bottom member 50. When bottom member 50 is inserted into capture slots 80, 82, rear side 54 may contact outer edges 21 of extensions 22, 23 and covers 24, 25 as seen in FIG. 1. Due at least partially to the contact, captures 20 may limit or prevent movement of bottom member 50 in third direction R'".

Figure 8:
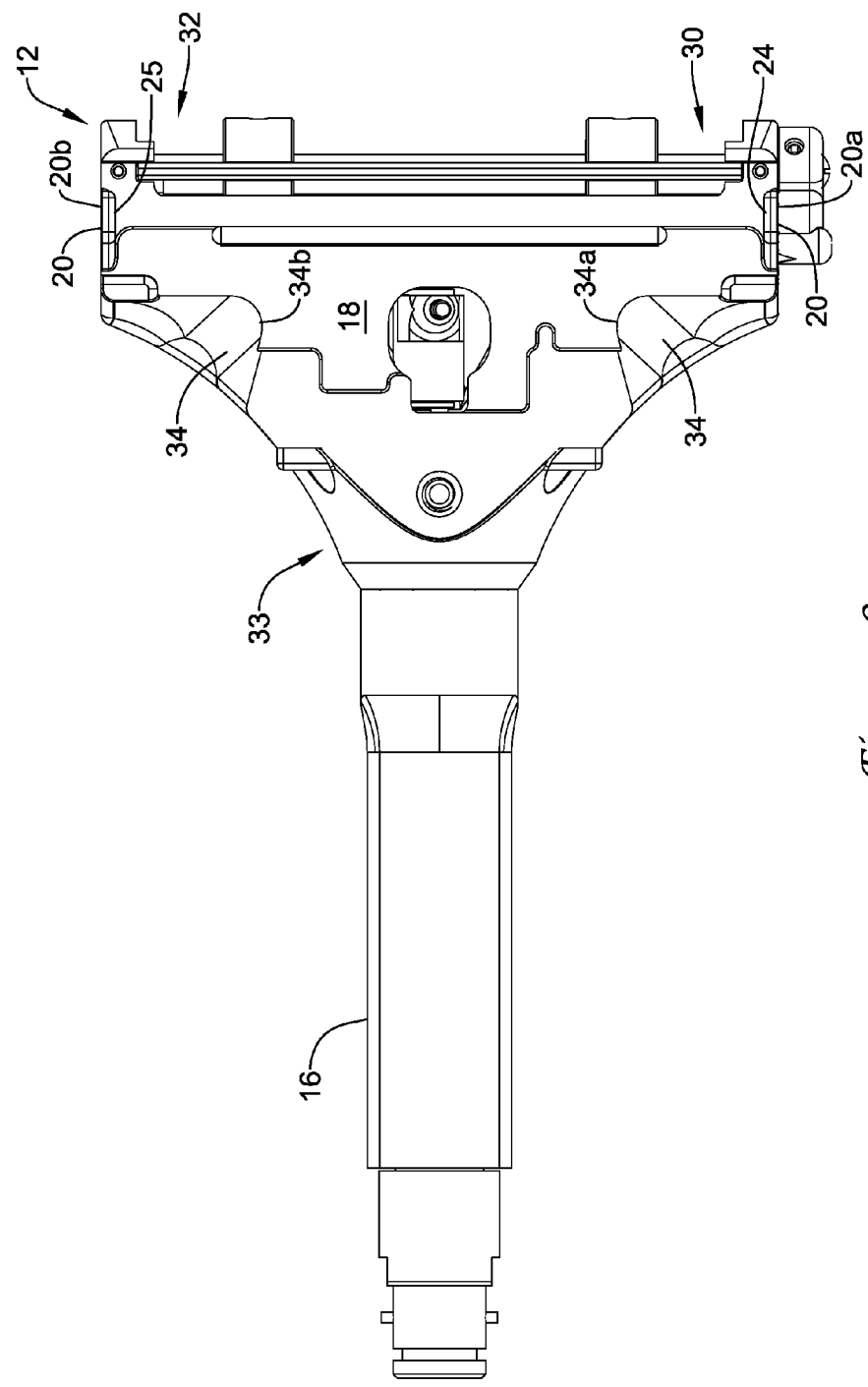
FIG. 8 is a bottom view of a main body of a dermatome according to an aspect of the disclosure.
Figure 9:
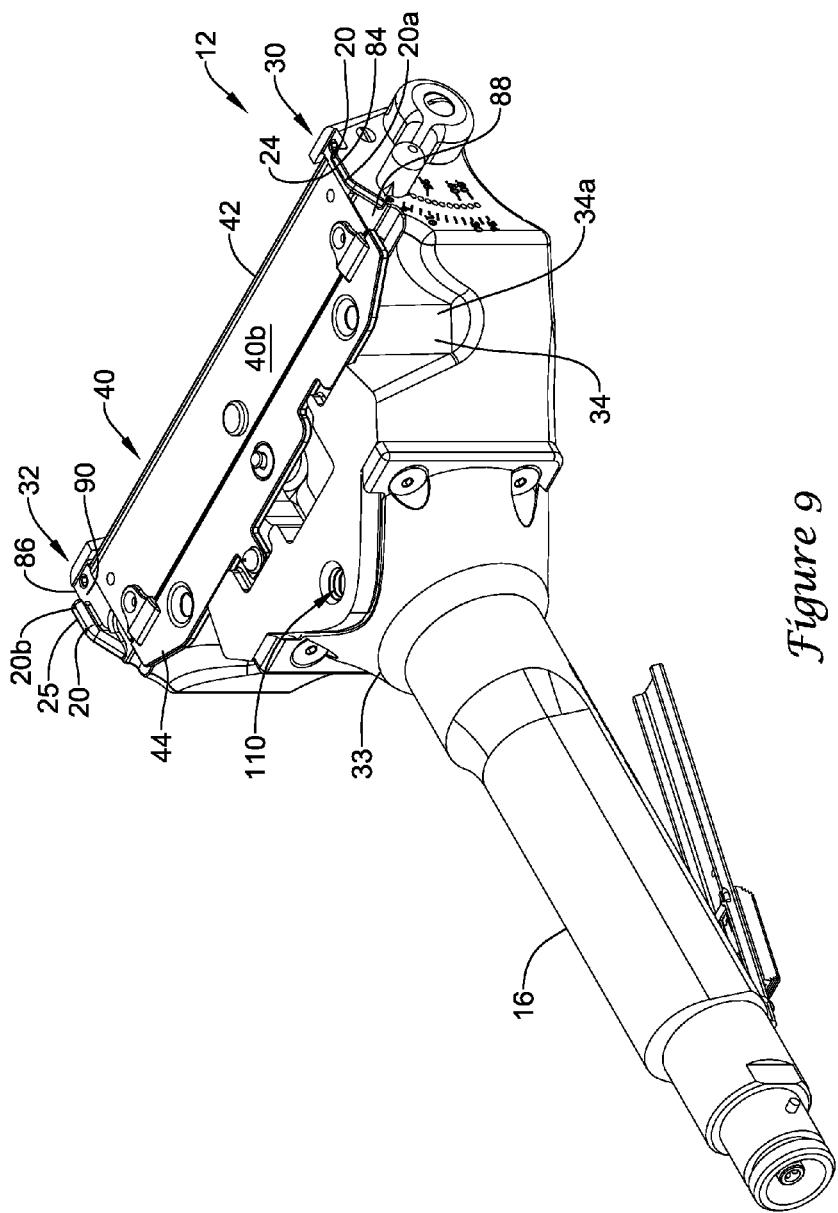
FIG. 9 is a side perspective view of a main body and blade assembly according to an aspect of the disclosure.

Main body 12 may take on any shape or size having captures 20 and capable of receiving blade assembly 40 and bottom member 50. For example, as seen in FIGS. 1-4 and 8, main body 12 may have a first side 30, second side 32 and bottom surface 18 where bottom surface 18 generally extends from first side 30 to second side 32. First side 30 and second side 30 may meet at a back portion 33 of main body 12 or first side 30 and second side 32 may be separated by a further side or handle 16, as seen in FIG. 8, or other object.

As seen in FIGS. 1-3, 8 and 9, main body 12 may have indents 34 formed therein and may include any desired number of indents 34 for the purpose of assisting in the removal of a mounted blade assembly or for any other purpose. For example, as depicted in FIG. 8, main body 12 may include a first indent 34*a* and a second indent 34*b*. First indent 34*a* may be any shape or size and may be at least partially defined by first side 30 and bottom side or surface 18. Second indent 34*b* may be any shape or size and may be at least partially defined by second side 32 and bottom side or surface 18. Indents 34 may be placed at any locations along bottom surfaces 18 and sides 30, 32 where a mounted blade assembly 40 at least partially covers a portion of at least one indent 34 defined by bottom surface 18. In an example, first indent 34*a* and second indent 34*b* may be spaced apart along bottom surface 18 of main body 12 so as to allow a user to insert a thumb in one indent and a forefinger (also known as an index finger) in a second indent simultaneously, where the user would press down with the inserted thumb and forefinger on a mounted blade assembly 40 for the purpose of separating the mounted blade assembly 40 from main body 12, or for any other purpose. Although a thumb and forefinger are mentioned in the example, any finger or tool may be used to apply a force or pressure to blade assembly 40 through one or more indents 34 in main body 12.

In FIG. 2, dermatome 10 is depicted in exploded view so as to show an illustrative assembly of main body 12, blade assembly 40 and bottom member 50. In the illustrative assembly, blade assembly 40 may be mounted onto main body 12 in any manner that may allow blade assembly to reciprocate in opposite lateral directions with respect to main body 12. For example, blade assembly 40 may be placed onto main body 12 and fastened thereto or blade assembly 40 may contact main body 12 in a non-fastened manner. After blade assembly 40 has been placed or mounted on main body 12, bottom member 50 (e.g., a width plate) may be inserted onto main body 12 so as to mount blade assembly 40 between bottom member 50 and main body 12. For example, at least one capture profile 56 of bottom member 50 may be inserted into at least one capture slot 80, 82 by moving the bottom member 50 generally in third direction R'. In the example, capture slots 80, 82 located on opposing sides of main body 12 or bottom surface 18 may each receive a capture profile 57, 59, respectively. In other words, bottom member 50 may be positioned on main body 12 and slid in third direction R'" such that capture profiles 56 of bottom member 50 are inserted into capture slots 80, 82 of captures 20 of main body 12 on opposing sides of bottom member 50.

Figure 10:
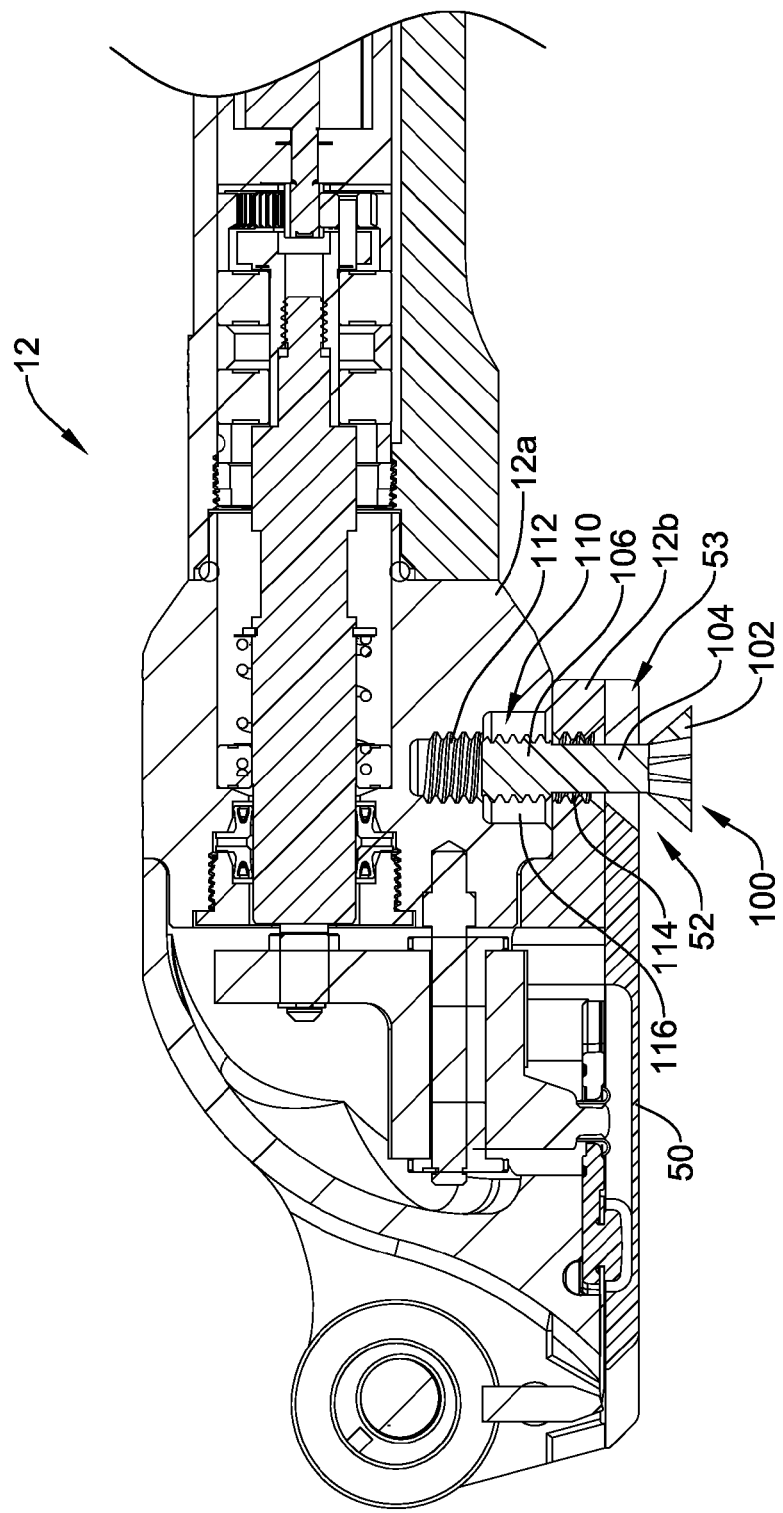
FIG. 10 is a cross-sectional view of the main body and bottom member of a dermatome according to an aspect of the disclosure.

Dermatome 10 may be designed such that bottom member 50 may be assembled onto and removed from main body 12 with fastener 100 retained with main body 12 of dermatome 10. Thus, medical personnel need not be concerned with accounting for fastener 100, as fastener 100 may remain coupled to main body 12, even when loosened to assemble and/or remove bottom member 50. For example, as shown in FIG. 10, main body 12 may include threaded bore 110 extending into main body 12 configured to receive fastener 100. Threaded bore 110 may include a first, inner threaded portion 112, a second, outer threaded portion 114, and an enlarged, unthreaded portion 116 positioned between inner threaded portion 112 and outer threaded portion 114. In other words, threaded bore 110 may include two stages of threaded separated by an unthreaded portion. In some instances, inner threaded portion 112 may be formed in a first component 12a of main body 12 and outer threaded portion 114 may be formed in a second component 12b of main body 12. Enlarged, unthreaded portion 116 may be formed in either first component 12a or second component 12b. Assembly of first component 12a with second component 12b orients inner threaded portion 112 axially with outer threaded portion 114 to define threaded bore 110.

Fastener 100 may include a head 102 and a shank extending from head having a threaded end portion 106 and an unthreaded portion 104 positioned between head 102 and threaded end portion 106. Unthreaded portion 104 of shank of fastener 100 may be sized to pass through slot 53 of fastening hole 52 (e.g., have a diameter smaller than width of slot 53 of fastening hole 52), while head 102 may be sized larger than fastening hole 52. Threaded end portion 106 of fastener 100 may be sized to threadably engage each threaded portion 112, 114 of threaded bore 110, while unthreaded portion 116 of bore 110 may have a diameter greater than major diameter of threaded end portion 106 of fastener 100. Thus, fastener 100 may be considered a captive screw coupled to main body 12 in both a threadably engaged configuration and a threadably disengaged configuration.

With such a configuration, prior to assembling bottom member 50 to main body 12, fastener 100 may be coupled to main body 12 with threaded end portion 106 captured in enlarged unthreaded portion 116 of bore 110. In this position, fastener 100 remains coupled to main body 12, since fastener 100 may not be removed from bore 110 without advancing threaded end portion 106 through outer threaded portion 114 of bore 110 through rotation of fastener 100. In this position, bottom member 50 may be positioned on main body 12 and slid in third direction R''' such that capture profiles 56 of bottom member 50 are inserted into capture slots 80, 82 of captures 20 while unthreaded portion 104 of shank of fastener 100 passes through slot 53 of fastening hole 52 of bottom member 50 in a lateral direction (e.g., perpendicular to longitudinal axis of fastening hole 52).

After bottom member 50 has been inserted into captures 20 along third direction R''', bottom member 50 may be restricted or limited in two, three or more directions. For example, after inserting bottom member 50 into captures 20, movement of bottom member in first and second lateral directions R', R'' and third direction R''' substantially perpendicular and substantially parallel to first and second directions R', R'' may be limited. In addition, after bottom member 50 has been inserted into captures 20, bottom member 50 may be fastened to main body 12. Bottom member 50 may be fastened to main body 12 through the use of fastener 100. For instance, fastener 100 may be rotated such that threaded end portion 106 threadably engages inner threaded portion 112 of bore 110 and is tightened to secure bottom member 50 to main body 12. As fastener 100 is tightened, head 102 of fastener 100 may bear against base member 50 to clamp base member 50 to main body 12. In some instances, one and only one fastener 100 may be utilized to fasten bottom member 50 to main body 12. Fastener 100 may be any type of fastener 100, such as a threaded fastener capable of being inserted into fastening hole 52 in bottom member 50 and capable of mating with complementary threads in a threaded hole in main body 12. Any other fastener capable of releasably connecting bottom member 50 with main body 12 may be utilized.

After bottom member 50 has been fastened or connected to main body 12, a user may desire to remove bottom member 50 from the connection and optionally remove blade assembly 40. In the configuration shown in FIG. 10, fastener 100 may be rotated to unthread threaded end portion 106 from inner threaded portion 112 of bore 110 such that threaded end portion 106 is fully disposed in enlarged unthreaded portion 116 of bore 110. Thus, in this position, fastener 100 may not be threadably engaged with threaded bore 110 yet still be captured in threaded bore 110 of main body 12 such that fastener 100 may be retained with main body 12. With fastener 100 loosened, base member 50 may be removed from main body 12 by sliding base member 50 in fourth direction R'''' to disengage capture profiles 56 from capture slots 80, 82 of captures 20 and move unthreaded portion 104 of fastener 100 laterally through slot 53.

In other instances, fastener 100 may be removed from communication with main body 12 and optionally, from communication with bottom member 50. For instance, if fastener 100 is a threaded fastener, fastener 100 may be unscrewed from the threaded bore 110 of main body 12 and pulled or unthreaded through fastening hole 52 of bottom member 50. After removing fastener 100, bottom member 50 may be removed from contact with main body 12 and blade assembly 40 by sliding, in at least direction R''''', bottom member 50 out of capture slots 80, 82 of captures 20a, 20b or any other captures 20. Once width plate or bottom member 50 has been removed from dermatome 10, blade assembly 40 may be optionally removed. Blade assembly 40 may be removed from being mounted on main body 12 by any means. For example, blade assembly 40 may be separated from main body 12 by applying pressure or a force to first side 40a of blade assembly 40. In the example, pressure or force may be applied to first side 40a through a user placing at least a finger or thumb or other instrument into at least one indent 34 defined by main body 12 and pressing that finger, thumb or other instrument against first side 40a. The requisite amount of force required to separate blade assembly 40 from main body 12 may vary depending on any number of factors. The amount of force required and the instrument(s) to be used may be determined by a user.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A dermatome, comprising:
  a main body including:
    a bottom surface; and
    a first capture and a second capture, the second capture spaced across the main body from the first capture; and
  a blade having a first side facing the bottom surface of the main body and a second side opposite the first side; and
  a bottom member facing the second side of the blade and communicating with the first and second captures;
  wherein the first and second captures extend from a bottom side of the main body; and
  wherein the first capture forms a first capture slot defined by:
    a first extension extending from the bottom side of the main body and forming a first lateral stop and a first back stop; and
    a first cover extending from a the first extension, and wherein the second capture forms a second capture slot defined by:
  a second extension extending from the bottom side of the main body and forming a second lateral stop and a second back stop; and
  a second cover extending from the second extension.

2. The dermatome of claim 1, wherein the bottom member is positioned within the first capture slot and within the second capture slot.

3. The dermatome of claim 2, wherein a rear side of the bottom member abuts the first and second captures.

4. The dermatome of claim 3, wherein a portion of the bottom member is interposed between the bottom side of the main body and the first cover of the first capture slot and the second cover of the second capture slot.

5. The dermatome of claim 2, wherein one and only one fastener fastens the bottom member to the main body.

6. The dermatome of claim 5, wherein the blade is mounted to the main body by the fastened bottom member.

7. The dermatome of claim 5, wherein the bottom member includes a fastener opening having a longitudinal axis and a slot, wherein the fastener is configured to be positioned in the fastener opening by passing the fastener through the slot in a direction generally perpendicular to the longitudinal axis.

8. The dermatome of claim 1, further comprising:
  a fastener fastening the bottom member to the main body.

9. The dermatome of claim 1, wherein the main body has a first side and a second side along opposite edges of a bottom side, and
  wherein a first indent is at least partially defined by the first side and the bottom side and a second indent is at least partially defined by the second side and the bottom side.

10. The dermatome of claim 9, wherein the blade is coupled to a blade mount to define a blade assembly;
  wherein the blade assembly abuts the bottom side, and
  wherein the blade assembly at least partially covers a portion of the first indent defined by the bottom side and at least partially covers a portion of the second indent defined by the bottom side.

11. The dermatome of claim 1, wherein the blade is coupled to a blade mount to define a blade assembly.

12. A dermatome comprising:
  a main body;
  at least one capture extending from the main body;
  a bottom member engaging the at least one capture, wherein the at least one capture prevents movement of the engaged bottom member in opposing first and second lateral directions and in at least a third direction substantially perpendicular to the first and second lateral directions; and
  at least one fastener fastening the bottom member to the main body;
  wherein a capture profile of the bottom member engages the at least one capture;
  wherein the at least one capture forms a capture slot having a bottom formed by a bottom side of the main body, a side, a top and a back, and
  wherein the capture profile is configured to abut the bottom, the side, the top and the back of the capture slot.

13. The dermatome of claim 12, wherein the at least one capture includes a first capture and a second capture, and
  wherein the bottom member engages the first and second captures.

14. The dermatome of claim 12, wherein the capture profile is received within the at least one capture and a stop of the bottom member abuts an outer surface of the at least one capture.

15. The dermatome of claim 12, further comprising a blade positionable between the main body and the bottom member.

16. The dermatome of claim 12, further comprising a blade assembly positionable between the main body and the bottom member.

17. The dermatome of claim 16, wherein the blade assembly includes a blade coupled to a blade mount.

18. The dermatome of claim 17, wherein the blade assembly reciprocates relative to the main body.

* * * * *

UNITED STATES PATENT AND TRADEMARK OFFICE
CERTIFICATE OF CORRECTION

| | | |
|---|---|---|
| PATENT NO. | : 8,608,755 B2 | Page 1 of 1 |
| APPLICATION NO. | : 13/180925 | |
| DATED | : December 17, 2013 | |
| INVENTOR(S) | : Mark Mahaffey and Bruce Straslicka | |

It is certified that error appears in the above-identified patent and that said Letters Patent is hereby corrected as shown below:

In the Specification

Column 6, Line 50: delete "R'" and insert -- R''' --.

Signed and Sealed this
Eleventh Day of March, 2014

Michelle K. Lee
*Deputy Director of the United States Patent and Trademark Office*